United States Patent [19]

Wallace

[11] 4,095,106
[45] June 13, 1978

[54] RADIATION ATTENUATION GAUGE WITH MAGNETICALLY COUPLED SOURCE

[75] Inventor: Steven A. Wallace, Knoxville, Tenn.

[73] Assignee: The United States of America as represented by the United States Department of Energy, Washington, D.C.

[21] Appl. No.: 778,196

[22] Filed: Mar. 16, 1977

[51] Int. Cl.² ............................................. G01N 23/00
[52] U.S. Cl. .................................. 250/358 R; 250/491
[58] Field of Search ................... 250/275, 308, 358 P, 250/358 R, 359, 360, 491, 493, 496

[56] References Cited

U.S. PATENT DOCUMENTS 3,492,477  1/1970  Arnesen ........................... 250/358 P Primary Examiner—Davis L. Willis
Attorney, Agent, or Firm—Dean E. Carlson; Stephen D. Hamel; Allen H. Uzzell

[57] ABSTRACT

A radiaton attenuation gauge for measuring thickness and density of a material comprises, in combination, a source of gamma radiation contained within a housing comprising magnetic or ferromagnetic material, and a means for measuring the intensity of gamma radiation. The measuring means has an aperture and magnetic means disposed adjacent to the aperture for attracting and holding the housed source in position before the aperture. The material to be measured is disposed between the source and the measuring means.

9 Claims, 3 Drawing Figures

RADIATION ATTENUATION GAUGE WITH MAGNETICALLY COUPLED SOURCE

BACKGROUND OF THE INVENTION

This invention was made in the course of, or under, a contract with the Energy Research and Development Administration.

It relates in general to radiation attenuation gauging and, more particularly, to an apparatus suited for measuring wall thickness and density of hollow objects.

The principle of radiation attenuation gauging is the relationship between the thickness and density of a material and its absorbtivity for gamma radiation. This relationship is given by the expression:

$$I_t = I_o e^{-(\mu/\rho)\rho d}$$

where:
$I_t$ = intensity of radiation transmitted through the sample
$I_o$ = intensity of incident radiation
$\mu/\rho$ = mass absorbtion coefficient
$\rho$ = density of sample
$d$ = thickness of material.

Since $\mu/\rho$ is a characteristic of the type of material, the logarithm of the intensity of transmitted radiation is inversely related to the product of the thickness and density of the sample. Accordingly, radiation attenuation gauging is capable of measuring the $\rho d$ product. If the sample is of constant thickness, an increase in transmitted radiation intensity corresponds to a decrease in density. Likewise, if the material is of constant density, an increase in transmitted radiation intensity corresponds to a decrease in thickness. Accordingly, radiation attenuation gauging measures both thickness and density of a material.

The chief application of radiation attenuation gauging is in quality control measurement. In such measurements the material composition is known and usually the density can be expected to be fairly constant. Fluctuations in transmitted radiation then corresponds to fluctuations in thickness. Radiation attenuation gauging is particularly useful for measuring homogeneity of nuclear properties of material such as targets, shielding, etc. Since the nuclear properties are dependent upon the number and construction of atoms in a given path length, $\rho d$ measurements are directly related.

PRIOR ART

A variety of devices for radiation attenuation measurements are available in the prior art. See, for example, U.S. Pat. No. 3,764,806 which describes a system for radiographic examination of pipe welds. A gamma source is transported inside the pipe by a self-propelled vehicle. Radiation passing through the pipe is detected and measured by external means. In order for such a system to be useful for thickness and density measurement, the gamma source and the radiation detector must be precisely positioned such that the radiation passes perpendicularly through the pipe wall. Without precise control of the source position, spurious measurements would result.

One prior art method of overcoming the difficulty of precise source control is described in U.S. Pat. No. 3,564,247. This method involves filling a hollow container with a radioactive gas. Since the density of the gas will be constant throughout the container, the intensity of radiation transmitted through the wall will be directly related to the wall $\rho d$ product. Such a method requires that the interior of the article being measured be completely enclosed, which would be impractical for measuring sheet material, etc. Furthermore, the use of gamma-emitting gases in industrial processes presents a serious hazard to personnel.

SUMMARY OF THE INVENTION

It is an object of this invention to provide an apparatus for measuring thickness and density of material which eliminates the need for servo-mechanisms to precisely control the position of the radiation source.

It is a further object to provide apparatus for measuring wall thickness and density of hollow objects without the use of radioactive gas.

It is an additional object to provide an apparatus for measuring thickness and density of material which is particularly adaptable to remote control operation.

These and other objects are accomplished in an apparatus for measuring thickness and density of a material comprising in combination:

a source of gamma radiation contained within a housing comprising magnetic or ferromagnetic material;

means for measuring the intensity of gamma radiation, said measuring means having an aperture for admitting radiation to be measured; and first magnetic means disposed adjacent the measuring means aperture and adapted to attract said housed source into a position before the aperture such that gamma radiation emitted by said source passes through the aperture and is measured by the measuring means.

The material to be measured is placed between the source and the measuring means. The magnetic means holds the source opposite the aperture as the material and measuring means are moved with respect to one another.

DETAILED DESCRIPTION

Figure 1:
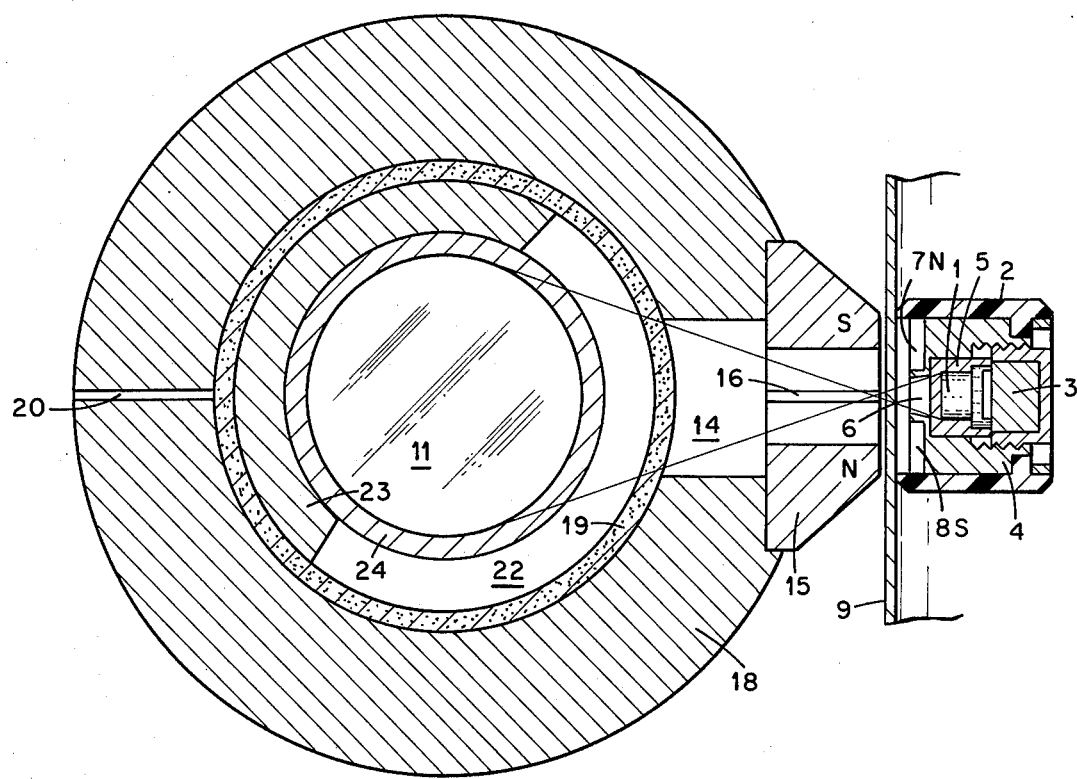
FIG. 1 is an enlarged horizontal cross-sectional view of an apparatus of this invention.

The apparatus of this invention utilizes the force of magnetic attraction to precisely position a housed gamma source before the aperture of a means for measuring gamma radiation. The means for measuring gamma radiation can be any conventional radiation detection means such as a scintillating material in combination with a photomultiplier tube or a photodiode, coupled with electronic circuitry for counting or integrating the number of incident photons. It is within the skill of the art to select or assemble a detector and circuitry suitable for measuring gamma radiation of a particular frequency and intensity. Examples of radiation detectors are described in *Sourcebook on Atomic Energy*, Samuel Glasstone, P. Van Nostrand Co., Inc., Princeton, N.J. (1967).

The detector of the measuring means has an aperture for admitting radiation to be measured. Magnetic means are disposed adjacent the aperture for attracting a magnetically-housed gamma source into a position before the aperture, such that radiation emitted from the source passes through the aperture to the detector. By "adjacent" it is meant that the magnetic means is disposed near the aperture in a suitable orientation to attract the housed source into position before the apertures, i.e., in front of the aperture, such that radiation emitted from the source enters the aperture and is detected by the detector.

The magnetic means can be either a permanent magnet or an electromagnet, however, spatial limitations encourage the use of permanent magnets. Any magnetic material may be used for the permanent magnet, such as iron, platinum-cobalt, ferrite, alnico, or samarium-cobalt. The preferred material is samarium-cobalt, $SmCo_5$. The magnet disposed adjacent the aperture of the detector can be oriented in any manner as to attract the source into position before the aperture. The preferred orientation of the permanent magnetic means is a tapered hollow cylinder mounted co-axially in front of the aperture of the measuring means. The hollow central portion of the cylinder corresponds with the dimemsions of the aperture so that the magnetic means functions as a collimator. The cylinder can be tapered or sized at the end away from the detector to correspond with the dimensions or spacing of magnetic or ferromagnetic material of the source housing. In a preferred embodiment, the magnet means has both north and south poles facing outward from the detector. By "facing outward" it is meant that north and south magnetic flux is directed outward from the detector. In this manner, the north and south poles of a magnetic source housing can be firmly held in the desired position.

The source of gamma radiation can be any of a large number of gamma-emitting isotopes. The amount needed for a particular application is governed by the intensity of radiation emitted. As is customary in the art, the selection of the gamma source will depend upon the sensitivity of the detector and counting means and upon the thickness of material to be measured. In addition, the safety of personnel and the amount of shielding required are to be considered.

The source housing comprises magnetic or ferromagnetic material. The housing must contain sufficient ferromagnetic or magnetic material to provide sufficient magnetic attraction force to enable the magnetic means associated with the detector to hold the housed source against the material being measured. The amount of magnetic or ferromagnetic material needed can be readily calculated from the weight of the housed source, the strength of permanent magnets and the thickness and magnetic permeability of the material to be measured. If the source were to be always disposed directly above the detector, as in the case where the detector and source are substantially stationary and the material to be measured is moved between them, then the entire weight of the source would no longer be borne by the magnetic field.

The source housing can be spherical or it can have one or more flat surfaces. Spherical housings allow the housed source to roll freely on the surface of material being measured. One disadvantage with spherical source housing is that a random error is introduced into the measurement if the gamma source should be slightly off-center within the housing. For this reason, it is preferred that the source housing have a flat surface which slides along the surface of the material being measured. The radiation from the source will then pass through the same amount of housing material for each measurement taken.

For the protection of personnel, it is preferred that the source be shielded as far as practicable by the housing. The housing is then provided with an aperture to permit the passage of a portion of the emitted radiation. The housing can also have magnetic means disposed against its aperture to ensure its proper orientation. In a preferred mode, housing is provided with magnetic material of both north and south poles facing outward from the source on either side of the aperture. These poles project north and south magnetic flux away from the source. When the permanent magnet associated with the radiation measuring means also projects north and south magnetic flux outward from the detector, the opposing poles of the housing and detector means are strongly attracted, bringing the source into the desired orientation with respect to the detector. The desired orientation is that in which the housing aperture communicates with the detector aperture so that substantially all the radiation passing through the housing aperture and through the material being measured passes through the detector aperture. In this manner the reproducibility of the measurements is greatly improved.

As used herein, the term aperture is not limited to openings, since gamma radiation penetrates matter. For purposes of this invention, apertures are regions of lower gamma absorbtivity than surrounding material, thereby transmitting gamma radiation. Accordingly, the apertures may be solid material such as beryllium or aluminum to prevent damage and contamination to the detector or source. Aperture material may be chosen to filter out lower energy radiation from spectra of the source.

PREFERRED EMBODIMENT

Figure 2:
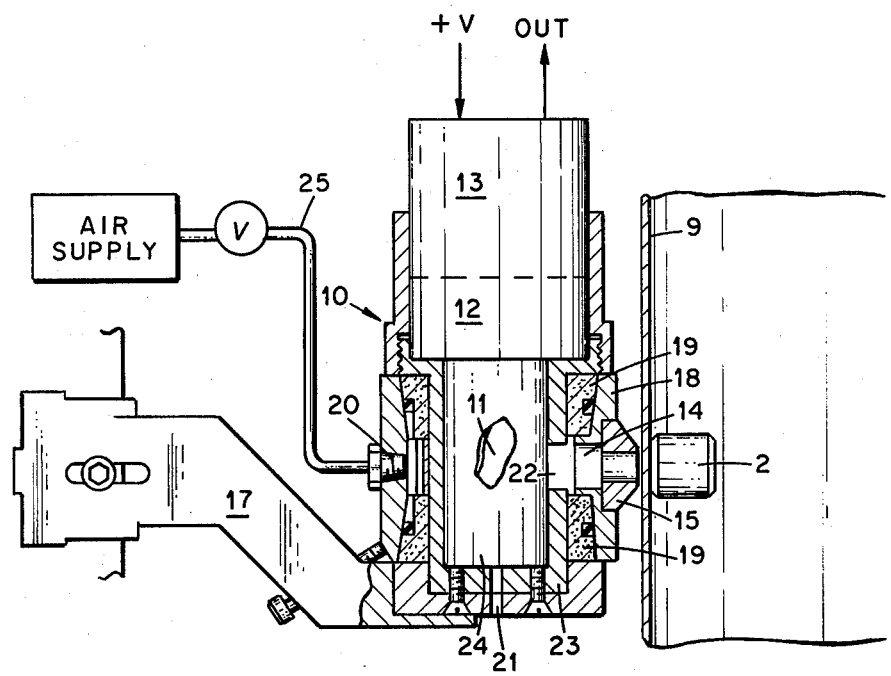
FIG. 2 is a vertical cross-sectional view of the apparatus of FIG. 1.

With reference to FIG. 1, the source 1 is surrounded by a cylindrical housing 2. The housing is coated with polytetrafluoroethylene to reduce friction and prevent scarring of the article being measured. The source can be $^{153}Gd$ or $^{133}Ba$, for example. The housing contains a lead shield 3 behind the source and additional shielding of a ferromagnetic W-3.5 wt.% Ni-1.5 wt.% Fe alloy, 4 around the circumference. The source is enclosed in a stainless steel casing 5. The housed source is unrestrained, other than by the magnetic field, and moves freely as the detector is moved. A housing aperture 6 permits passage of emitted radiation. Adjacent the aperture are two permanent magnets 7N and 8S having north and south poles facing outward such that north and south pole magnetic flux is directed away from the source. The housed source is disposed on the opposite side of the material being measured 9 from the detector. Also referring to FIG. 2, the means for measuring radiation comprises a detector 10 consisting of a scintillation material 11, in this case $CaF_2$, in combination with photodiode 12. Electronic circuitry 13, for example a picoammeter (Analog Devices AD515L), receives input current from the photodiode and outputs a voltage proportional to the radiation incident to the photodiode. This output signal proportion to the incident radiation is provided to additional electronic circuitry (not shown). The detector has aperture 14 for admitting radiation to be measured. In front of and adjacent the aperture 14 is magnetic means 15 which is a tapered cylinder $SmCo_5$ permanent magnet, with the smaller portion facing outward from the measuring means. The permanent magnet is split and separated by a shim of magnetic steel, 16. One half of the magnet is a north pole and the other half is a south pole so that both north and south pole magnetic flux are directed away from the detector. The surface of the magnet facing away from the detector corresponds in width with the spacing of the permanent magnets 7N and 8S mounted on the source housing. In this manner, centering of the source before the aperture is assured.

The entire means for measuring radiation is pin-supported by bracket 17. Radiation shield 18 contains aperture 14 and is held in position by an air bearing comprising cylindrical porous carbon bushings 19 disposed coaxially with radiation shield 18 between the scintillation crystal 11 and the radiation shield. The flexible hose 25, air inlet 20, and air outlet 21 permit passage of air through the porous bushings 19. During operation, air or other gaseous fluid is passed through the porous bushings with sufficient velocity to allow free rotation of the floating radiation shield 18, and thereby the aperture 14, with respect to the radiation detecting means. The porous bushings 19 are located on both sides of slot 22 in inner radiation shield 23 which allows passage of radiation passing through the aperture 14 to scintillation material 11 and permits measurements with 180° rotation of aperture 14. A single porous bushing with a slot for the passage of radiation can be used if desired. Porous gas bearings used in this apparatus are more fully described in U.S. Pat. No. 3,721,479. The scintillation material is surrounded by an aluminum light shield 24 which prevents external light from contaminating the output of the scintillation material. The use of such shields is customary in scintillation detectors. Normally, the interior of the light shield has white oxide coating, e.g. MgO on the interior to provide diffused reflectivity. When an article is to be measured, the source and measurement means are placed on opposite sides and either the measurement means and/or the article is moved. When measurements are taken at various points along the surface of the article, the air bearing assembly permits rotation of the aperture to coincide with the surface of the article. The housed source likewise moves on the other side of the article. The freely moving source and the freely rotating aperture ensure precise positioning of the source aperture 6 before the detector aperture 14. When hollow articles such as spheres, cylinders, etc. are measured, the source is normally to be placed on the inside of the article. The air bearing permits rotation of the aperture 14 without the need for servo-mechanisms to maintain the respective orientation of the permanent magnet 15 and the source housing 2. It can be readily seen the use of magnetic attraction to maintain the source and detector in precise relationship substantially simplifies the apparatus.

Figure 3:
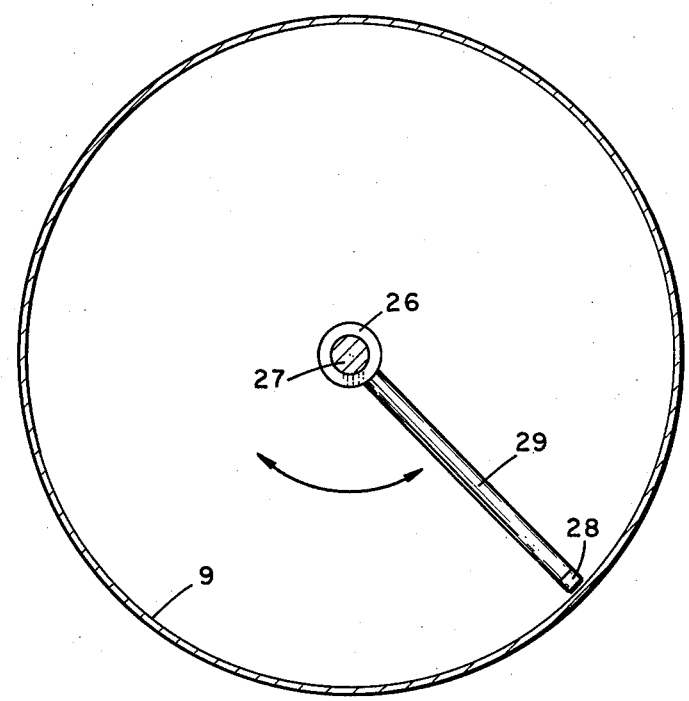
FIG. 3 is a top view of a cylinder containing a tethered radiation source.

As an alternative to allowing the source housing to move along the surface, possibly scarring or damaging the surface of the article or the housing, the source housing can be restrained on a flexible or mechanical tether such as shown in FIG. 3. The housed source 28 is attached to radial rod 29 secured by slip ring 26 to axial rod 27. The length of rod 29 is such that the housing never contacts the inner surface of the article being measured, cylinder 9. The mechanical tether can be any arrangement of mechanical elements which permits movement of the source and is adapted to position the source before the measuring means aperture without the source contacting the surface of material being measured. The mechanical tether is preferably adapted to permit the magnetic source to move freely under the influence of the detector magnet means, and maintained at a constant distance from the interior surface of the article being measured. For example, if the article were a hemisphere, the mechanical tether can be a radial rod secured by a pin to the center of a freely rotatable turntable. The source would be mounted at the end of the radial rod. It can be readily appreciated that suitable mechanical tether arrangements can be devised for practically any shape of surface being measured. If desired, the source can be supported along one or more axis with the magnetic force urging the source into the proper orientation. As shown in FIG. 1, the proper orientation is achieved with that particular source when substantially all of the radiation passing through housing aperture 6 passes through measurement means aperture 14.

It will be apparent to those skilled in the art that a variety of magnetic configurations are capable of attracting and holding the source housing in the proper position before the aperture of the measuring means, and such configurations are to be regarded as equivalents of those specifically described herein:

What is claimed is:

1. An apparatus for measuring thickness and density of a material comprising in combination:
   a source of gamma radiation contained within a housing comprising magnetic or ferromagnetic material;
   means for measuring the intensity of gamma radiation, said measuring means having an aperture for admitting radiation to be measured; and
   magnetic means disposed adjacent said aperture of said measuring means, said housed source being held by magnetic attraction in a position before said aperture such that gamma radiation from said source passes through said aperture and is measured by said measuring means.

2. The apparatus of claim 1 in which said housing fis spherical.

3. The apparatus of claim 1 in which the magnetic means disposed adjacent said measuring means aperture has both north and south poles facing outward from said measuring means, and said source housing comprises permanent magnetic material disposed such that said housing has both a north pole and a south pole facing outward from said source.

4. The apparatus of claim 3 in which said housing has a flat external surface comprising both a north pole and a south pole facing outward from said source.

5. The apparatus of claim 3 in which said housing has an aperture for transmitting radiation emitted from said source, and said north and south poles of said housing are positioned adjacent said housing aperture such that the north and south poles of the magnetic means disposed adjacent the measurement means aperture attract the housing into an orientation in which the housing aperture communicates with the measurement means aperture.

6. The apparatus of claim 1 in which said housing has a flat external surface.

7. The apparatus of claim 1 further comprising a mechanical tether attached to said source to position said source before said measuring means aperture without said source contacting the surface of material being measured.

8. The apparatus of claim 7 in which said mechanical tether permits said source, under the influence of said magnetic means, to move freely within an article being measured, at a constant distance from the interior surface of said article.

9. The apparatus of claim 1 in which said measuring means comprises a scintillation material, a cylindrical radiation shield surrounding said scintillation material and having an aperture for admitting radiation to be measured, a porous cylindrical bushing coaxial with said radiation shield and disposed between said scintillation material and said radiation shield, and means for passing a gaseous fluid through said porous bushing with sufficient velocity to allow free rotation of said cylindrical shield whereby said aperture is freely rotatably with respect to said scintillation material.

* * * * *